United States Patent [19]

McCarty

[11] Patent Number: 5,582,839
[45] Date of Patent: Dec. 10, 1996

[54] MAGNESIUM TAURATE AND OTHER MINERAL TAURATES

[75] Inventor: Mark F. McCarty, San Diego, Calif.

[73] Assignee: Nutrition 21, San Diego, Calif.

[21] Appl. No.: 423,891

[22] Filed: Apr. 18, 1995

[51] Int. Cl.$^6$ ............................. A61F 2/02; A61K 9/14; A61K 9/20; A61K 9/48
[52] U.S. Cl. ..................... 424/489; 424/423; 424/451; 424/464; 424/474; 514/937
[58] Field of Search .................................. 424/423, 451, 424/464, 474, 489; 514/937

[56] References Cited

U.S. PATENT DOCUMENTS 3,725,553  4/1973  Giotti et al. ........................... 514/578

OTHER PUBLICATIONS

B. M. Altura et al. (1984) Magnesium, electrolyte transport and coronary vascular tone. Drugs 28 (Suppl. 1):120–142.
T. W. Anderson et al. (1975) Ischemic heart disease, water hardness and myocardial magnesium. CMA Journal 113:199–203.
S. E. Atahanov et al. (1992) Modulation of receptor–dependent increase of calcium ions in human platelets by taurine. Arzneim.–Forsch./Drug Res. 42(11):1311–1313.
J. Azuma et al. (1983) Double–blind randomized crossover trial of taurine in congestive heart failure. Current Therap. Res. 34(4):543–557.
T. Dyckner et al. (1983) Effect of magnesium on blood pressure. Brit. Med. Jour. 286:1847–1848.
K. R. Geiβ et al. (1994) The effect of a taurine–containing drink on performance in 10 endurance–athletes. Amino Acids 7:45–56.
K. C. Hayes et al. (1989) Taurine modulates platelet aggregation in cats and humans[1-3]. Am. J. Clin. Nutr. 49–1211–1216.
R. J. Huxtable (1992) Physiological actions of taurine. Physiological Reviews 72(1):101–163.
L. T. Iseri (1984) Magnesium in coronary artery disease. Drugs 28 (Suppl. 1):151–160.
T. Motoyama et al. (1989) Oral magnesium supplementation in patients with essential hypertension. Hypertension 13(3):227–232.
M. A. Petty et al. (1990) The effects of taurine on atherosclerosis development in cholesterol–fed rabbits. European Jour. of Pharmacology 180:119–227.
M. P. Ryan et al. (1984) The role of magnesium in the prevention and control of hypertension. Ann. Clin. Res. 16:81–88.
S. W. Schaffer et al. (1994) Mechanisms underlying physiological and pharmacological actions of taurine on myocardial calcium transport. Taurine in Health and Disease 171–180.
S. W. Schaffer et al. (1990) Regulation of calcium homeostasis by taurine: role of calmodulin. Taurine: Functional Neurochemistry, Physiology, and Cardiology 217–225.
M. S. Seelig et al. (1974) Magnesium interrelationships in ischemic heart disease: a review. The Amer. Jour. of Clin. Nutrition 27:59–79.
M. Shechter et al. (1992) The rationale of magnesium supplementation in acute myocardial infarction. Arch. Intern. Med. 152:2189–2196.
K. Yamauchi–Takihara et al. (1986) Taurine protection against experimental arterial calcinosis in mice. Biochemical and Biophysical Research Communications 140(2):679–683.

*Primary Examiner*—Carlos Azpuru
*Attorney, Agent, or Firm*—Knobbe, Martens, Olson & Bear

[57] ABSTRACT

A magnesium–taurine compound and its method of synthesis. the compound is synthesized by reacting taurine and magnesium in a 2:1 molar ratio. The resulting mixture is diluted with methanol and the remaining clear filtrate is crystallized from methanol. This compound may be administered orally as a nutritional supplement or may be administered orally or intravenously for the therapeutic or prophylactic treatment of acute cardiac conditions.

7 Claims, No Drawings

MAGNESIUM TAURATE AND OTHER MINERAL TAURATES

FIELD OF THE INVENTION

The present invention relates to the synthesis and use of complexes comprising biologically available mineral taurates. More specifically, the invention relates to the synthesis of magnesium taurate and its use as a nutritional supplement and therapeutic agent.

BACKGROUND OF THE INVENTION

Magnesium is nutritionally important for maintenance of vascular integrity, but is often deficient in fatty, refined modern diets (Seelig et al., *Am. J. Clin. Nutr.*, 27:59–79, 1974). Deleterious vascular effects of magnesium deficiency include cardiac arrhythmias and hypertension (Anderson et al., *Can. Med. Assoc. J.*, 113:199–203, 1975). Magnesium supplements have been shown to reduce such hypertension (Dyckner et al., *Brit. Med. J.*, 286:1847–1849, 1983; Motoyama et al., *Hypertension*, 113:227–232, 1989; Ryan et al., *Ann. Clin. Res.*, 16:81–88, 1984). Intravenous administration of magnesium salts in the treatment of acute myocardial infarction has been found to decrease the subsequent incidence of arrhythmias and to improve survival. Intravenous magnesium also exerts a therapeutic effect in hypertensive crises and intractable arrhythmias (Ryan et al., 1984; Iseri, *Drugs*, 16:81–88, 1984; Shechter et al., *Arch. Intern. Med.*, 152:2189–2196, 1992).

Intracellular magnesium, usually in complex with ATP, is an essential cofactor, usually in a complex with ATP, for numerous enzymes including energy-dependent membrane transport proteins such as the sodium/potassium ATPase and the calcium ATPase (Altura et al., *Drugs*, 28(Suppl. 1):120–142, 1984. Significant intracellular magnesium deficiency impairs the activity of these transporters, resulting in decreased intracellular levels of potassium, and increased intracellular levels of sodium and calcium.

Taurine is an amino acid present in high concentrations in excitable and secretory tissue. Its role in cardiac function has received particular attention (Huxtable, *Physiol. Rev.*, 72:101–163, 1992; Schaffer et al., *Taurine in Health and Disease*, pp. 171–180, 1994). Although taurine can be synthesized endogenously from the amino acid cysteine, in mammals it is derived principally from the diet and is thus considered a "conditionally essential" nutrient. Conventional diets supply 40–400 mg of taurine daily, while vegetarian diets are extremely low in this amino acid (Huxtable, 1992).

The main function of taurine in mammals appears to be the regulation of transmembrane ionic movements, especially the regulation of calcium distribution (Schaffer et al., 1994; Huxtable, 1992; Schaffer et al., *Taurine: Functional Neurochemistry, Physiology and Cardiology*, pp. 217–225, 1990). However, the mechanisms of this regulation are not well understood. Taurine also exerts an anti-atherogenic action in animal models of atherosclerosis or arterial calcinosis (Petty et al., *Eur. J. Pharmacol.*, 180:119–127, 1990; Yamauchi-Takihara et al., *Biochem. Biophys. Res. Commun.*, 140:679–683, 1986). Taurine has also been shown to moderate blood pressure increases and thus may have a clinical antihypertensive effect.

Taurine exerts a platelet stabilizing effect both in vitro and, after oral administration, ex vivo (Hayes et al., *Am. J. Clin. Nutr.*, 49:1211–1216, 1989; Atahanov, *Arzneim-Forsch/Drug Res.*, 42:1311–1313, 1992). Acute intravenous administration of taurine reduces the incidence of arrhythmias in animals treated with arrhythmogenic agents and multi-gram doses have been shown to be effective in the treatment of ischemic congestive heart failure (Azuma et al., *Curr. Ther. Res.*, 34:543–557, 1983). Thus, increased taurine intake appears to be beneficial to vascular health.

To insure optimal magnesium status, magnesium supplements are frequently advisable. Magnesium supplements are especially important for diabetics, as these individuals typically display reduced intracellular, plasma and bone levels of magnesium. Magnesium oxide is commonly used as a dietary supplement, although the bioavailability of the magnesium in this salt is far from optimal. Soluble magnesium salt complexes with good nutritional availability, including citrate and glycinate, typically are low in magnesium, the majority of the complex consisting of the counteranion which has no nutritional utility. There is a need in the art for a magnesium supplement in which the magnesium is complexed with a counteranion which itself has nutritional utility and would complement the vascular-protective actions of magnesium. The present invention addresses this need.

SUMMARY OF THE INVENTION

The present invention provides a compound having the formula $(H_2N-CH_2-CH_2-SO_3^-)_2\ X^{2+}$, wherein X is a divalent metal cation. Preferably, X is calcium or zinc; most preferably, X is magnesium.

Another embodiment of the invention is a method for providing a divalent mineral nutrient to a mammal, comprising orally administering to the mammal a divalent mineral taurate. Preferably, the divalent metal cation is magnesium. The magnesium taurate may be in the form of a salt or a complex. The divalent metal cation may also be calcium or zinc. The compound is advantageously administered in a daily dosage of between about 2 grams and about 7 grams; however the most preferred daily dosage is about 4.5 grams. According to a further aspect of this embodiment, the nutrient is administered in the form of a tablet or capsule.

The present invention also provides a method of treating an acute or chronic cardiac condition in a patient comprising parenterally administering to the patient an effective therapeutic amount of magnesium taurate. Advantageously, the compound is administered intravenously and the acute cardiac condition is myocardial infarction. According to another aspect of this embodiment, the effective therapeutic dosage is between about 200 mg/hour and about 1500 mg/hour; most preferably, it is between about 500 mg/hour and about 1000 mg/hour.

DETAILED DESCRIPTION OF THE INVENTION

The present invention provides a magnesium taurate salt and a magnesium taurate complex for the nutritional and therapeutic administration of magnesium and taurine, both of which are beneficial to vascular health. The reaction of taurine with magnesium oxide, magnesium hydroxide or magnesium salts, under appropriate conditions, yields products containing magnesium and taurine. Under alkaline conditions, taurine has a net negative charge and may form both a salt and a complex with magnesium in which two molecules of taurine associate with one atom of magnesium as depicted below.

| SALT | COMPLEX |

These compounds may be used both as a source of the essential nutrient magnesium and as a source of the conditionally essential amino acid taurine. The oral administration of these compounds delivers magnesium and taurine to appropriate sites of action. The magnesium-taurine compounds are also useful as therapeutic agents for congestive heart failure, acute myocardial infarction or other acute cardiac conditions associated with an increased risk for arrhythmias or congestive failure, as well as chronic disorders including essential hypertension, diabetes, insulin resistance syndrome and bronchospasm. Thus, the administration of magnesium taurate may have prophylactic as well as therapeutic applications.

The magnesium taurate salt of the invention is highly soluble in water and provides good nutritional availability of both magnesium and taurine. The complex form is insoluble in water, but will slowly dissolve in water as a result of its conversion to the salt form. The complex and salt forms are thus interchangeable. The dissolution of the complex form in water is greatly accelerated in the presence of acid.

The acute anti-arrhythmic effect of both magnesium and taurine, as well as taurine's ability to control congestive heart failure, suggests that this complex is of particular benefit in the management of acute ischemic cardiac episodes when administered intravenously. A daily dose providing the full U.S. recommended daily allowance (RDA) of magnesium (400 mg) would concurrently provide about 4.1 g taurine—well within the range demonstrated to be therapeutically effective in congestive heart failure.

The magnesium taurate protocol is described in Example 1. Magnesium hydroxide and taurine are mixed and heated in water. Most of the water is removed by evaporation, and then alcohol is added to precipitate the product and allow it to be separated by filtration.

Since two taurine molecules combine with one magnesium atom, it is preferred that the molar ratio of taurine to magnesium be about 2:1, although ratios of between about 1.5:1 and about 2.5:1 are contemplated. NMR analysis confirms the presence of taurine in the product. The product is extremely water-soluble. Surprisingly, the product is also stable to precipitation in the presence of additional alkali or in the presence of additional carbonate, thus illustrating the unexpected stability of this magnesium-containing compound.

For oral administration as a nutritional supplement, the compound may be provided as a tablet, aqueous or oil suspension, dispersible powder or granule, emulsion, hard or soft capsule, syrup or elixir. Compositions intended for oral use may be prepared according to any method known in the art for the manufacture of pharmaceutical compositions and such compositions may contain one or more of the following agents: sweeteners, flavoring agents, coloring agents and preservatives. The sweetening and flavoring agents will increase the palatability of the preparation. Tablets containing the magnesium taurate in admixture with non-toxic pharmaceutically acceptable excipients suitable for tablet manufacture are acceptable. Such excipients include inert diluents such as calcium carbonate, sodium carbonate, lactose, calcium phosphate or sodium phosphate; granulating and disintegrating agents, such as corn starch or alginic acid; binding agents such as starch, gelatin or acacia; and lubricating agents such as magnesium stearate, stearic acid or talc. Tablets may be uncoated or may be coated by known techniques to delay disintegration and absorption in the gastrointestinal tract and thereby provide a sustained action over a longer period of time. For example, a time delay material such as glyceryl monostearate or glyceryl distearate alone or with a wax may be employed.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil.

Aqueous suspensions may contain the magnesium taurate complex of the invention in admixture with excipients suitable for the manufacture of aqueous suspensions. Such excipients include suspending agents, dispersing or wetting agents, one or more preservatives, one or more coloring agents, one or more flavoring agents and one or more sweetening agents such as sucrose or saccharin.

Oil suspensions may be formulated by suspending the active ingredient in a vegetable oil, such as arachis oil, olive oil, sesame oil or coconut oil, or in a mineral oil such as liquid paraffin. The oil suspension may contain a thickening agent, such as beeswax, hard paraffin or cetyl alcohol. Sweetening agents, such as those set forth above, and flavoring agents may be added to provide a palatable oral preparation. These compositions may be preserved by an added antioxidant such as ascorbic acid. Dispersible powders and granules of the invention suitable for preparation of an aqueous suspension by the addition of water provide the active ingredient in admixture with a dispersing or wetting agent, a suspending agent, and one or more preservatives. Additional excipients, for example sweetening, flavoring and coloring agents, may also be present.

Syrups and elixirs may be formulated with sweetening agents, such as glycerol, sorbitol or sucrose. Such formulations may also contain a demulcent, a preservative, a flavoring or a coloring agent.

The magnesium taurate preparations for parenteral administration may be in the form of a sterile injectable preparation, such as a sterile injectable aqueous or oleaginous suspension. This suspension may be formulated according to methods well known in the art using suitable dispersing or wetting agents and suspending agents. The sterile injectable preparation may also be a sterile injectable solution or suspension in a non-toxic parenterally-acceptable diluent or solvent, such as a solution in 1,3-butanediol. Suitable diluents include, for example, water, Ringer's solution and isotonic sodium chloride solution. In addition, sterile fixed oils may be employed conventionally as a solvent or suspending medium. For this purpose, any bland fixed oil may be employed including synthetic mono or diglycerides. In addition, fatty acids such as oleic acid may likewise be used in the preparation of injectable preparations.

The pharmaceutical compositions may also be in the form of oil-in-water emulsions. The oily phase may be a vegetable oil, such as olive oil or arachis oil, a mineral oil such as liquid paraffin, or a mixture thereof. Suitable emulsifying agents include naturally-occurring gums such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsions may also contain sweetening and flavoring agents.

In a preferred embodiment, the amount of the complex administered orally is between about 2 g and about 7 g daily, corresponding to between approximately 200 mg and 600 mg magnesium, the remainder being taurine. In a particularly preferred embodiment, the amount of the complex administered daily is about 4 g, corresponding to about 400 mg magnesium. The preferred administration schedule for delivery of 400 mg magnesium would be two tablets, twice daily; if one were to ingest another high-availability source of magnesium plus straight taurine to achieve analogous benefits, eight tablets daily would be needed which is hardly optimal from a compliance standpoint.

For therapeutic or prophylactic use in myocardial infarction or other acute cardiac condition, the magnesium taurate complex is solubilized in an aqueous saline solution and administered parenterally. Although various administration routes including, for example, intramuscular, subcutaneous, intraperitoneal and intraarterial are contemplated, the preferred route is intravenous administration. The amount administered will depend on the weight of the patient and the severity of the condition, although contemplated doses for such administration will typically be from about 200 mg/hr to about 1500 mg/hr for a time sufficient to result in improvement of the condition. In a particularly preferred embodiment, this amount is between about 500 mg/hr and about 1000 mg/hr. Alternatively, the magnesium taurate may be administered in a bolus dose over a shorter period of time. Such dose is preferably greater than 5 grams once per day.

Although the synthesis and use of magnesium taurate is described herein, it is evident that other divalent mineral nutrients may also be complexed with taurine for oral administration as a nutritional supplement or for intravenous or oral administration as a therapeutic or prophylactic agent. Such essential nutrients include, for example, calcium and zinc, although other nutrients are also within the scope of the invention. Calcium is essential for preservation of bone density and in lowering blood pressure in some individuals, while zinc promotes efficient cell growth, wound healing, effective immune function and membrane stabilization.

The RDA for calcium is about 800 mg per day and that for zinc is about 15 mg per day. It is not required that the calcium taurate complex provide the entire daily amount of calcium as this will require about 10 g of taurine, but could be used to provide a portion of the RDA. The zinc RDA could be provided by a zinc taurate complex containing about 15 mg of zinc and about 200 mg taurine.

It is also evident that many variations of the synthetic scheme described below may be used to generate the compounds of the present invention. Any such scheme resulting in production of a divalent cation-taurine complex is within the scope of the present invention.

EXAMPLE 1

SYNTHESIS OF MAGNESIUM TAURATE

A mixture of magnesium hydroxide (9.50 g, 8.62 mmol) and taurine (2.16 g, 17.2 mmol) in 20 ml water was refluxed for 7 hours, then evaporated under vacuum to remove most of the water. The paste was diluted with 10 ml ethanol, and after two hours the solid was collected by filtration and dried. Magnesium taurate was obtained as a white powder (about 99% yield). Magnesium taurate could also be obtained as a white powder by lyophilization or by further drying of the paste remaining after evaporation of the reaction mixture.

Magnesium taurate obtained by this reaction scheme is a variable mixture of the complex form and the salt form. The salt form rapidly dissolves in water, leaving behind a solid that is primarily the complex form. The complex form dissolves more slowly in water as it converts to the salt form.

Preparation of magnesium taurate salt is described in the following example.

EXAMPLE 2

SYNTHESIS OF MAGNESIUM TAURATE SALT

Magnesium turnings (96.0 mg, 4 mmol; Aldrich, St. Louis, Mo.) were stirred in 10 ml methanol until completely reacted and dissolved. The excess methanol was evaporated, leaving solid magnesium methoxide. To the solid magnesium methoxide was added a solution of taurine (1 g, 8 mmol; Aldrich) in water (10 ml). The reaction mixture was vigorously stirred to form a clear solution, then heated to boiling and refluxed for 10–15 minutes. The solution was allowed to cool to room temperature, resulting in a milky colloidal solution which was then evaporated to dryness under vacuum to produce a white solid. Water (10 ml) and then methanol (20 ml) were then added to the resulting residue. After 2–3 hours with occasional shaking, the remaining undissolved white solids were removed by filtration. This material (about 50% yield) consisted of a small amount of taurine and magnesium salts, and an amorphous form of the magnesium taurate complex. The clear filtrate was evaporated to a wet paste which was slowly diluted with methanol (about 10 ml) until crystallization appeared complete. The yield of crystalline magnesium taurate was about 50% (about 0.45–0.60 g). The melting point (decomposition) was about 300°.

To verify the proposed structure of the resulting magnesium taurate salt, an elemental analysis was performed as follows.

EXAMPLE 3

ELEMENTAL ANALYSIS

A sample of the product from Example 1 was analyzed for % C, H, N and S by combustion and for % Mg by atomic absorption spectroscopy. The following results were obtained.

| Element | value | value for dihydrate |
| --- | --- | --- |
| % C | 16.38 | 15.57 |
| % H | 5.00 | 5.23 |
| % N | 9.09 | 9.08 |
| % S | 20.43 | 20.78 |
| % Mg | 6.25 | 7.88 |

These results are consistent with a chemical formula of $C_4H_{12}MgN_2O_6S_2 \cdot 2H_2O$ and a molecular weight of 308.61. This formula and molecular weight are consistent with a 2:1 taurine to magnesium ratio as diagrammed hereinabove. The product holds water tenaciously, as only 11–12% of the water is lost after 2 hours at 120° C.

To further confirm the presence of taurine in the crystalline compound, the product of Example 2 was analyzed by proton, carbon, and magnesium magnetic resonance spectroscopy as described below.

EXAMPLE 4

SPECTROSCOPY STUDIES

A sample of the salt was dissolved in deuterium oxide and analyzed in a 500 MHz Brucker Proton Multinuclear Resonance Spectrometer Model AM-500. The spectrum showed a symmetrical, closely-spaced multiplet centered at about 3.11 ppm and an HDO signal at 4.8 ppm. The multiplet is consistent with a second-order splitting between the two methylene groups of taurine, both of which are shifted downfield relative to the signals of free (zwitterionic) taurine ($^+H_3N-CH_2CH_2SO_3^-$) in water.

Signals due to zwitterionic taurine are undetectable. The protein magnetic resonance spectrum of free taurine in deuterium oxide shows two symmetrical triplets, centered at 3.49 and 3.32 ppm (coupling constant J=6.6), consistent with first-order splitting between the two sets of methylene protons. The $^{13}C$ spectrum of the salt in deuterium oxide, measured in the same instrument (Brucker AM-500), shows signals at 39.71 ppm ($H_2N-CH_2-$) and at 54.59 ppm ($-O_3S-CH_2$). The $^{25}Mg$ spectrum of the salt in deuterium oxide, measured in the same instrument, shows a single signal at exactly the same shift as $MgCl_2$. There is no evidence for the presence of any other magnesium species, such as covalent complexes, in the aqueous solution.

EXAMPLE 5

ALTERNATIVE SYNTHESIS OF MAGNESIUM TAURATE SALT

A mixture of magnesium hydroxide (433 mg, 7.46 mmol; Aldrich) and taurine (1.87 g, 14.9 mmol) in 20 ml water was heated under reflux for seven hours. The resulting milky mixture was allowed to cool, diluted with 40 ml methanol and allowed to stand overnight at room temperature. A white powder, consisting mostly of magnesium taurate complex, was removed by filtration. The clear filtrate was concentrated under vacuum to a pasty slurry, then diluted slowly with 10 ml methanol. After 2 hours, crystalline magnesium taurate salt was obtained by filtration. The yield was 940 mg (41%). The melting point (decomposition) was about 300° C. This salt was identical to that obtained in Example 2.

The magnesium taurate salt when dissolved in water resulted in a clear, colorless solution. When a concentrated aqueous solution was heated to boiling, the mixture became milky and then formed a fine white precipitate of the complex. Upon cooling, the precipitate redissolved, forming a clear solution of the salt.

A dilute suspension of the complex in water has a pH of about 9–10, and dissolves slowly to give a clear solution of the salt. The complex dissolves more readily if acid is added, and dissolution is very rapid at pH values below 5.

The synthetic scheme for calcium and zinc taurates will be essentially similar to Example 5, with the exception that either calcium or zinc hydroxide would be reacted with the taurine in the first step of the reaction scheme to ultimately form calcium and zinc taurate, respectively. The formation of other divalent mineral taurates by variations to the synthetic schemes described in Examples 1, 2, and 5, such variations being known to the skilled artisan, is also within the scope of the present invention.

The above detailed description of the invention is set forth solely to assist in understanding the invention. It is to be understood that variations of the invention, including all equivalents now known or later developed, are to be considered as falling within the scope of the invention, which is limited only by the following claims.

What is claimed is:

1. A method of treating an acute or chronic cardiac condition in a patient in need thereof, comprising parenterally administering to said patient an effective therapeutic dosage of magnesium taurate.

2. The method of claim 1, wherein said magnesium taurate is a pharmaceutically acceptable salt.

3. The method of claim 1, wherein said magnesium taurate is a complex.

4. The method of claim 1, wherein said compound is administered intravenously.

5. The method of claim 1, wherein said acute cardiac condition is myocardial infarction.

6. The method of claim 1, wherein said effective therapeutic dosage is between about 200 mg/hour and about 1500 mg/hour.

7. The method of claim 6, wherein said effective therapeutic dosage is between about 500 mg/hour and about 1000 mg/hour.

* * * * *